United States Patent [19]
Ohkawa et al.

[11] Patent Number: 5,608,104
[45] Date of Patent: Mar. 4, 1997

[54] IMMUNOLOGICAL DETECTION METHOD OF PYRETHROID COMPOUND, HAPTENIC COMPOUND, INTERMEDIATE FOR THE HAPTENIC COMPOUND, IMMUNOGEN AND ANTIBODY

[75] Inventors: Hideo Ohkawa, Hyogo-ken; Koji Kitajima, Chiba-ken; Kenji Kodaka, Chiba-ken; Yasunori Fumoto, Chiba-ken; Takako Kumeta, Chiba-ken, all of Japan

[73] Assignee: Mitsui Toatsu Chemicals, Inc., Tokyo, Japan

[21] Appl. No.: 310,772

[22] Filed: Sep. 27, 1994

[30]   Foreign Application Priority Data

Sep. 28, 1993  [JP]  Japan .................................. 5-241037

[51] Int. Cl.$^6$ ........................................... C07C 65/00
[52] U.S. Cl. ..................... 562/473; 556/441; 556/445; 560/64; 560/18; 568/648
[58] Field of Search ............................. 562/473; 560/64, 560/18; 568/648; 556/441, 445

[56]              References Cited

FOREIGN PATENT DOCUMENTS

| | | |
|---|---|---|
| 0235000 | 9/1987 | European Pat. Off. . |
| 0344816 | 12/1989 | European Pat. Off. . |
| 4329952 | 8/1994 | Germany . |
| WOA90/ 10450 | 9/1990 | WIPO . |

*Primary Examiner*—Paul J. Killos
*Attorney, Agent, or Firm*—Burns, Doane, Swecker & Mathis

[57]               ABSTRACT

Described is a detection method of a pyrethroid compound which comprises providing a first antibody against the pyrethroid compound, said first antibody having been obtained by immunizing a responder with an immunogen which is a first conjugate between a first carrier and a first haptenic compound represented by the following formula (1) or (2):

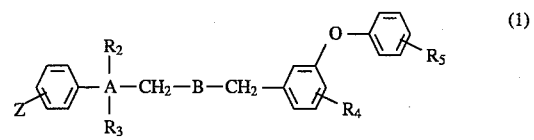

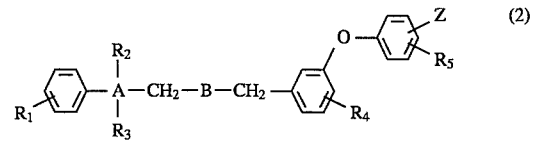

mixing the first antibody with the sample solution, causing any unreacted portion of the first antibody to be bound on a second conjugate as a coated antigen, said second conjugate being formed of a second carrier and a second haptenic compound and having been coated on a surface of a solid phase carrier, whereby an antigen-antibody conjugate is obtained; and reacting the antigen-antibody conjugate with a second antibody against the first antibody, said second antibody having a labelled enzyme linked therewith.

This invention has made it possible to conduct easy, economical and quick analysis of a pyrethroid compound contained in our surroundings such as water or soil, plants or foods.

2 Claims, No Drawings

IMMUNOLOGICAL DETECTION METHOD OF PYRETHROID COMPOUND, HAPTENIC COMPOUND, INTERMEDIATE FOR THE HAPTENIC COMPOUND, IMMUNOGEN AND ANTIBODY

BACKGROUND OF THE INVENTION

1. Field of the Invention

This invention relates to an antibody capable of undergoing specific linkage with a pyrethroid compound, a novel compound useful as a hapten for the preparation of the antibody (which may hereinafter be called a "haptenic compound"), a novel compound useful as an intermediate for the synthesis of the haptenic compound, an immunogen composed of the haptenic compound, and preparation processes thereof; and a method for the detection and measurement of one or more pyrethroid compounds in a sample by the use of the antibody.

2. Description of the Related Art

As immunochemical analyses of pyrethroid compounds, there are "Study on Antibodies specific to S-Bioallethrin" [J. Agric. Food Chem., 26, 1328–1333(1978)] and "Radioimmunoassay" [Experimentia, 35, 1619–1620(1679)], both reported by B. D. Hammock et al. These are fundamental studies on the application of an immunochemical analysis to a specific pyrethroid.

There is also a report by L. H. Stanker et al. of a basic study on the immunochemical analysis of permethrin in meat [J. Agric. Food Chem., 37, 834–839(1989)]. According to the report, three monoclonal antibodies were isolated by oxidizing dimethylvinyl groups of phenothrin with ozone into a carboxylic acid derivative, binding the derivative with a protein to obtain a hapten-protein conjugate and immunizing a responder with the conjugate. These antibodies, however, are only useful for the detection of phenothrin, permethrin, cypermethrin and deltamethrin and have very low detection sensitivity to other synthetic pyrethoids. When an antibody is reacted to a compound to be detected, a water-soluble organic solvent such as acetonitrile is added to increase the solubility of the compound in a sample so that the compound is rendered more reactive. In consideration of the stability of the antibody against the organic solvent, the concentration of the solvent must be controlled low, that is, at 6% or lower, leading to the unresolved problems that compounds having extremely low water solubility can hardly be detected and solvent removal or concentration is indispensable similarly to other micro analyses.

There is a growing social concern with the problem of pesticide residue in our living environment, particularly, with the ever increasing problem of post harvest application of pesticides in imported foods. In order to secure the safety of the living environment, it is necessary to precisely and promptly measure the amount of each pesticide remaining in a number of samples from the environment and foods.

Pesticide residues have heretofore been measured primarily by gas chromatography or high-performance liquid chromatography. These methods, however, are accompanied with such drawbacks that they require considerable labor and time for the preparation of a sample for analysis and measuring instruments, reagents and the like are costly. There is accordingly a desire for the development of a new, easy, economical and quick measuring method.

Pyrethroid compounds, which are targets of the analysis according to the present invention, are general-purpose insecticides having a wide spectrum so that they have been used widely for the control of sanitary insects found in grain, fruits, vegetables, cotton, coffee beans, tea leaves, animals, woods and home. The application field of pyrethroid compounds has been widening because of their lower toxicity against mammary animals and stronger effects for the control of insecticide-resistant insects compared with many other insecticides. The pyrethroid compounds each has a legally-imposed permissible upper limit on its residual amount in most foods. In addition, many pyrethroid compounds have strong toxicity against aquatic animals so that their influence to the environment is worried.

SUMMARY OF THE INVENTION

Samples from our surroundings and foods which require analysis of a pesticide residue are expected to steadily increase from now on. A primary object of the present invention is therefore to provide an easy, economical and quick method for the analysis of one or more pyrethroid compounds in such samples. It is the present situation that the analysis of a pesticide residue in imported agricultural products by the conventional methods is no longer feasible in cost and labor in view of the number of samples which will increase from no on due to an increase in the number of pesticides to be subjected to regulations. The present invention hence has a great contribution to such a situation. By utilizing the method of the present invention, it is also possible to check the type and level of each pesticide in a sample before analysis of components of the pesticide residue. The present invention has thus solved the above-described many problems, including those related to the analysis of imported agricultural products, by overcoming the defect of the conventionally-produced antibodies, that is, their instability against an organic solvent, thereby increasing the number of pyrethroid compounds detectable by the enzyme-linked immunosorbent assay method (hereinafter called the "ELISA method" for the sake of brevity).

According to the present invention, the amount of one or more pyrethroid compounds remaining in water or soil in our surroundings, plants or foods can be measured easily and quickly.

DETAILED DESCRIPTION OF THE INVENTION & PREFERRED EMBODIMENTS

With a view toward providing a solution to the above problems, the present inventors have carried out an investigation on immunochemical analysis of pyrethroid compounds. As a result, it has been found that pyrethroid compounds contained in our surroundings and food samples can be detected easily and quickly by employing an indirect competitive ELISA method, leading to the completion of the invention.

In a first aspect of this invention, there is thus provided a detection method of a pyrethroid compound contained in a sample solution, which comprises:

providing a first antibody against the pyrethroid compound, said first antibody having been obtained by immunizing a responder with an immunogen which is a first conjugate between a first carrier and a first hapetenic compound represented by the following formula (1) or (2):

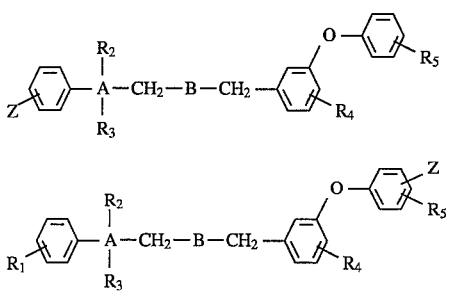

(1)

(2)

wherein $R_1$ represents a hydrogen atom, halogen atom, $C_{1-5}$ alkyl group, $C_{1-5}$ haloalkyl group, $C_{1-5}$ alkoxyl group, $C_{1-5}$ haloalkoxyl group, $C_{1-5}$ alkylthio group, $C_{1-5}$ haloalkylthio group, $C_{2-5}$ alkenyl group, $C_{2-5}$ haloalkenylthio group, $C_{2-5}$ alkinyl group, $C_{2-5}$ haloalkinyl group, lower-alkoxy-lower-alkyl group, lower-alkoxyl-lower-alkoxyl group, $C_{2-5}$ haloalkenyloxy group, $C_{2-5}$ alkinyloxy group, $C_{1-5}$ alkoxycarbonyl group, $C_{1-5}$ haloalkoxycarbonyl group, $C_{3-6}$ cycloalkyl group, $C_{3-6}$ cycloalkoxyl group, phenyl group, phenoxy group or cyano group; $R_2$ represents a $C_{1-5}$ alkyl group or $C_{1-5}$ haloalkyl group, $R_3$ represents a hydrogen atom, $C_{1-5}$ alkyl group or $C_{1-5}$ haloalkyl group, and $R_2$ and $R_3$ may be coupled together to form a $C_{3-6}$ cycloalkyl group or $C_{3-6}$ cyclohaloalkyl group; $R_4$ and $R_5$ and $R_5$ individually represent a hydrogen atom, halogen atom, alkyl group or alkoxyl group; A represents a carbon atom or silicon atom; B represents —$CH_2$—, —$NR_6$—, —O— or —S—; $R_6$ represents a hydrogen atom or lower alkyl group; and Z represents —Y—$(CH_2)$m-COOH or —Y—$(CH_2)$n-$NH_2$, Y represents —$H_2C$—, —$NR_7$—, —O— or —S—, $R_7$ represents a hydrogen atom or lower alkyl group, and m and n individually stand for 1–5;

mixing the first antibody with the sample solution, causing any unreacted portion of the first antibody to be bound on a second conjugate as a coated antigen, said second conjugate being formed of a second carrier and a second haptenic compound and having been coated on a surface of a solid phase carrier, whereby an antigen-antibody conjugate is obtained; and reacting the antigen-antibody conjugate with a second antibody against the first antibody, said second antibody having a labelled enzyme linked therewith.

In a second aspect of this invention, there are also provided novel haptenic compounds represented by the above formulas (1) and (2), respectively.

In a third aspect of this invention, there are also provided novel intermediates for the preparation of the haptenic compound of the formula (1) or (2), said intermediates being represented by the following formulas (3) and (4):

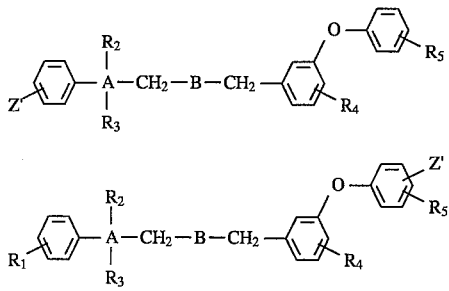

(3)

(4)

wherein $R_1$ represents a hydrogen atom, halogen atom, $C_{1-5}$ alkyl group, $C_{1-5}$ haloalkyl group, $C_{1-5}$ alkoxyl group, $C_{1-5}$ haloalkoxyl group, $C_{1-5}$ alkylthio group, $C_{1-5}$ haloalkenylthio group, $C_{2-5}$ alkinyl group, $C_{2-5}$ haloalkenylthio group, $C_{2-5}$ alkinyl group, $C_{2-5}$ haloalkinyl group, lower-alkoxyl-lower-alkyl group, lower-alkoxyl-lower-alkoxyl group, $C_{2-5}$ haloalkenyloxy group, $C_{2-5}$ alkinyloxy group, $C_{1-5}$ alkoxycarbonyl group, $C_{1-5}$ haloalkoxycarbonyl group, $C_{3-6}$ cycloalkyl group, $C_{3-6}$ cycloalkoxyl group, phenyl group, phenoxy group or cyano group; $R_2$ represents a $C_{1-5}$ alkyl group or $C_{1-5}$ haloalkyl group, $R_3$ represents a hydrogen atom, $C_{1-5}$ alkyl group or $C_{1-5}$ haloalkyl group, and $R_2$ and $R_3$ may be coupled together to form a $C_{3-6}$ cycloalkyl group or $C_{3-6}$ cyclohaloalkyl group; $R_4$ and $R_5$ individually represent a hydrogen atom, halogen atom, alkyl group or alkoxyl group; A represents a carbon atom or silicon atom; B represents —$CH_2$—, —$NR_6$—, —O— or —S—; $R_6$ represents a hydrogen atom or a lower alkyl group; and Z' represents —Y'—$(CH_2)$m-$COOR_7$' or —$(CH_2)$n-$NHR_8$, Y' represents —$CH_2O$—, —$NR_9$—, —O— or —S—, $R_7$' represents a $C_{1-5}$ alkyl group, lower-alkoxyl-lower-alkyl group, lower-alkoxyl-lower-alkoxyl-lower-alkyl group, lower-alkylthio-lower-alkyl group, tetrahydrofuranyl group, phenyl group, phenyloxy-lower-alkyl group, phenacyl group, diacylmethyl group, N-phthalimido methyl group, benzyl group or silyl group; m stands for 1 to 5, $R_8$ represents a formyl, acetyl, haloacetyl, propionyl, phenylacetyl, alkoxycarbonyl, haloalkoxycarbonyl, fluorenemethylcarbonyl, phenyloxycarbonyl, phenylthiocarbonyl, piperidinyloxycarbonyl or benzyloxycarbonyl group, $R_9$ represents a hydrogen atom or a lower alkyl group, and n stands for 1 to 5.

In a fourth aspect of this invention, there is also provided a novel hapten-carrier conjugate which contains the novel haptenic compound of the formula (1) or (2).

In a fifth aspect of this invention, there is also provided a novel antibody against pyrethroid compounds, said antibody having been obtained by immunizing a responder with the conjugate as an immunogen.

In a sixth aspect of this invention, there is also provided a detection method of a pyrethroid compound in which method the first antibody is employed as an antibody.

In a seventh aspect of this invention, there is also provided a measuring method of a pyrethroid compound in which method the antibody is reacted with the pyrethroid compound.

The determination method of pyrethroid compounds according to the present invention will hereinafter be described more specifically. First, an antibody against pyrethroid compounds, which has been obtained by immunizing a responder with a hapten-carrier conjugate (protein or the like as a carrier), is prepared as a first antigen. A predetermined excess amount of the first antibody is mixed with a sample solution containing one or more pyrethroid compounds and they are reacted. Any unreacted portion of the first antibody which portion has still remained in the reaction mixture is caused to be bound on a coated antigen which has been coated on a solid phase carrier. Then, the resulting antigen-antibody conjugate, which has been bound with the solid phase carrier, is reacted with a labeled-enzyme-linked second antigen. A buffer solution containing a chromogenic reagent which develops a color by an enzymatic reaction of the labeled enzyme is thereafter added to the reaction mixture to develop a color, followed by the measurement of the absorbance. The concentration of the one or more pyrethroid compounds is calculated from the measured absorbance based on a calibration curve.

The first antigen employed in the above method may be obtained by using as an immunogen the conjugate between a carrier such as a protein and haptenic compounds of the present invention.

Examples of the compounds usable as haptenic compounds in the present invention include many compounds which vary depending on the combination of various substituents in the formula (1). Preferred examples include those containing a carbon atom as A and an oxygen atom as B. More preferred examples include those containing a carbon atom as A, an oxygen atom as B, methyl groups as $R_2$ and $R_3$, respectively and in Z, an oxygen atom as Y. The most preferred one is the compound which contains a hydroxycarbonylmethyloxy group as Z, methyl groups as $R_2$ and $R_3$, respectively, a carbon atom as A, an oxygen atom as B and hydrogen atoms as $R_4$ and $R_5$, respectively.

Concerning the compound represented by the formula (2), many can be exemplified similarly. Preferred examples include those containing a carbon atom as A and an oxygen atom as B and in Z, an oxygen atom as Y. Most preferred are those containing an alkoxyl or haloalkoxyl group as $R_1$, methyl groups as $R_2$ and $R_3$, respectively, hydrogen atoms as $R_4$ and $R_5$, respectively, a carbon atom as A, an oxygen atom as B and a 4-hydroxycarbonylmethyloxy group as Z.

The haptenic compounds exemplified above can be prepared from the above-described compound represented by the formula (3) or (4). The compounds of the formula (1) and (2) can be obtained by subjecting the compounds of the formula (3) and (4) to reduction or hydrolysis in the presence of a base or an acid. A number of compounds represented by the formulas (3) and (4) can be illustrated according to the combination of various substituents. Most preferred examples include those containing a methoxycarbonylmethyloxy group as Z', methyl groups as $R_2$ and $R_3$, respectively, a carbon atom as A, an oxygen atom as B, and hydrogen atoms as $R_4$ and $R_5$, respectively.

These intermediates (3) and (4) can be prepared from known compounds.

The compound of the formula (3) can be prepared by subjecting a compound represented by the formula (5):

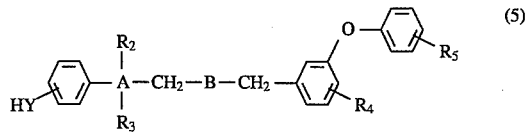

wherein A, B, Y and $R_2$ to $R_5$ have the same meanings as described above and a compound represented by the formula (6):

X—(CH$_2$)$_m$COOR$_7$'  (6)

wherein X represents a halogen atom and m and $R_7$' have the same meanings as described above to condensation in the presence of a base.

The compound of the formula (3) can also be prepared by subjecting the compound represented by the formula (5) and a compound represented by the following formula (7):

X—(CH$_2$)$_n$NHR$_8$  (7)

wherein X represents a halogen atom and n and $R_8$ have the same meanings as described above to condensation in the presence of a base.

The compound of the formula (4), on the other hand, can be prepared by subjecting a compound represented by the formula (8):

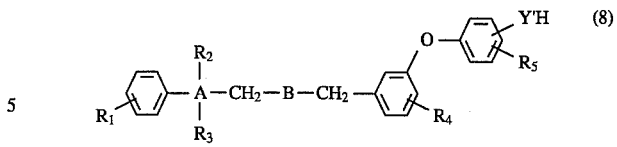

wherein $R_1$ to $R_5$, A, B and Y' have the same meanings as described above and the compound represented by the formula (6) or (7) to condensation in the presence of a base.

Among the compounds of the formula (5) which are usable as raw materials for the preparation of the intermediates, those containing a carbon atom as A and an oxygen atom as B can easily be obtained from the known compound disclosed in Japanese Patent Laid-Open Nos. 32840/1983 or 77836/1983 or by applying a known process to the preparation of the raw material compounds.

In addition, the compounds of the formula (5) containing carbon atoms as A and B, respectively, can be prepared by a known reaction of the known compound disclosed in Japanese Patent Laid-Open No. 201835/1987. For example, by reacting a compound represented by the following formula (9):

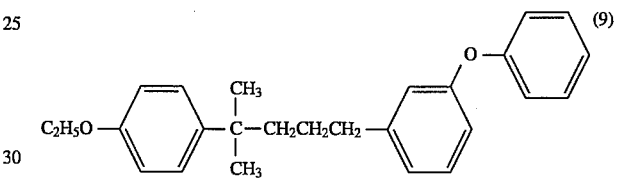

with a base (for example, a strong base such as potassium tertiary-butoxide) in a polar organic solvent, a corresponding phenol derivative can be prepared.

The compound of the formula (5) containing a silicon atom as A can be prepared by a known reaction using a known organic silicon compound, said reaction and silicon compound having been disclosed in Japanese Patent Laid-Open Nos. 263988/1986 and 106032/1987. For example, by reacting a compound represented by the following formula (10):

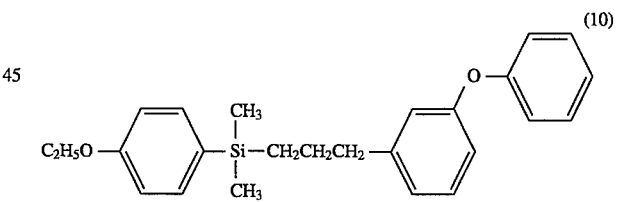

with a base (for example, a strong base such as potassium tertiary-butoxide) in a polar solvent, a corresponding phenol derivative can be prepared.

Among the compounds of the formula (8) which are usable as raw materials for the preparation of the other intermediate, those containing a carbon atom as A and an oxygen atom as B can easily be obtained from the known compound or in accordance with the preparation process for the known compound, said known compound and process having been disclosed in Japanese Patent Laid-Open Nos. 32840/1983 or 77836/1983.

In addition, the compounds of the formula (8) which contain carbon atoms as A and B, respectively can be prepared by the known reaction of the known compounds disclosed in Japanese Patent Laid-Open No. 201835/1987 For example, by treating a methoxymethoxy group of the compound represented by the following formula (11):

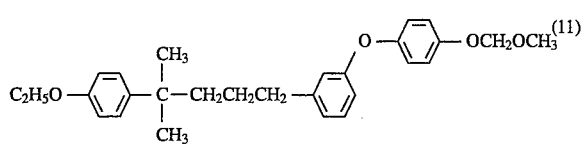

with an acid, a corresponding phenol derivative can be prepared. The compound of the formula (11) can be prepared by subjecting the compounds represented by the following formulas (12) and (13):

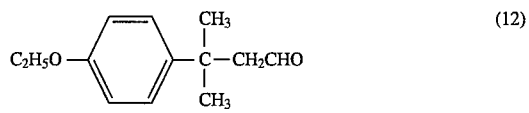

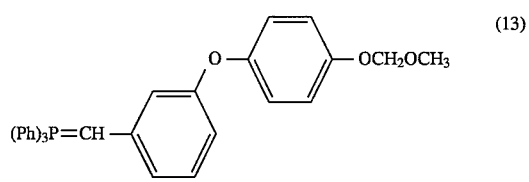

to condensation, followed by catalytic reduction.

The compounds containing a silicon atom as A can be prepared by the known reaction using the known organic silicon compound, said reaction and silicon compound having been disclosed in Japanese Patent Laid-Open Nos. 263988/1986 and 106032/1987. For example, by treating a methoxymethoxy group of the compound represented by the following formula (14):

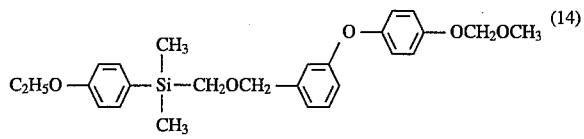

with an acid, a corresponding phenol derivative can be prepared. The compound of the formula (14) can easily be prepared by subjecting the compounds represented by the following formulas (15) and (16):

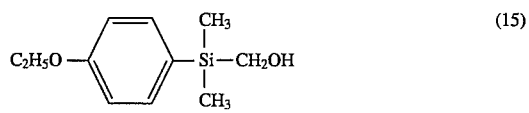

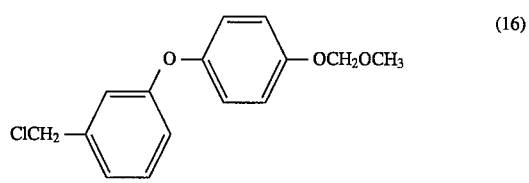

to condensation in the presence of a base.

An immunogen for producing a first antibody can be prepared by subjecting the haptenic compound of the formula (1) or (2) and a carrier (for example, serum protein such as albumin, globulin and hemocyanin, azophenyl acetic acid, a glutamine-adenine-tyrosine copolymer) to condensation in the presence of a binding reagent. Particularly when the haptenic compound is a carboxylic acid derivative, it is the common practice to bind the haptenic compound with a protein in accordance with the mixed acid anhydride method [J. Biol. Chem., 234, 1090–1094(1959)] proposed by B. F. Erlanger et al.

Any solid phase carrier commonly employed in the ELISA method can be used in the detection method of the present invention. It can be used in various shapes. Examples of the shape include a tube, a well plate, a micro plate, an elongated stick, a thin strip and beads. Illustrative examples of the material which forms the surface of the solid phase include polystyrene or other suitable plastics, nitrocellulose, nylon, polyvinylidene difluoride, glass and silica. Although no particular limitation is imposed on the solid phase carrier, a 96-well microtiter plate made of polystyrene is suited.

In the measuring method according to the present invention, the antigen may be coated on a surface of the solid phase carrier by diluting, with a buffer solution for coating, a conjugate between the haptenic compound and a responder's serum albumin which conjugate produces a first antibody, adding the diluted solution to a solid phase carrier and then conducting incubation. As the buffer solution for coating, a 10 mM phosphate buffer solution (pH 7.5, 100 mM NaCl) is suitably employed. No particular limitation is, however, imposed insofar as the buffer solution contains a surfactant or the like which disturbs the coating.

As a protein for the second conjugate, proteins other than those usable for the immunogen can also be employed. The conjugate can be prepared in the same manner as described above in the preparation of the immunogen. The antigen may be coated on the solid phase carrier under the following conditions: The suitable concentration of the antigen is 0.01–0.1 μg/ml. When a 96-well microtiter plate is employed, it is desired to use the antigen in an amount of about 0.1 mg/well. Incubation may preferably be carried out at 4° C. overnight.

After having the antigen absorbed on the solid phase carrier, it is necessary to block the antigen-free portions with a protein other than the antigen in order to prevent non-specific binding of the antibody. This blocking can be effected by adding a 3% skim milk solution to the solid phase carrier and then incubating them at 25° C. for one hour. After the incubation, the carrier is washed with a washing buffer. A 10 mM phosphate buffer solution (pH 7.2, 0.8% NaCl, 0.02% KCl and 0.02% "Tween 20") is suited as the washing buffer.

One of the features of the measuring method according to the present invention is that the reaction between a pyrethroid compound and the first antibody can be conducted easily by adding an organic solvent of a high concentration to the reaction system. The solubility of the pyrethroid compound in water is generally very low so that it cannot be reacted efficiently with the first antibody under the ordinary conditions. As a result of studying various conditions, it has been found that the addition of an organic solvent of a certain group to the reaction system makes it possible to promote the reaction between an antibody and a pyrethroid compound. Examples of the organic solvent to be added include water-soluble organic solvents such as alcohols, e.g., methanol and ethanol and dimethyl sulfoxide, N,N-dimethylformamide, N,N-dimethylacetamide, hexa-methylphosphoramide, N,N-dimethyl imidazolidinone, acetonitrile and acetone. Judging from the stability of the first antibody in an organic solvent, methanol and its concentration of 20% to 50% are suited but not limited thereto. The first antibody may be diluted with a diluting buffer [10 mM phosphate buffer (pH 7.2), 0.8% NaCl, 0.02% KCl] to give its concentration in the reaction mixture, for example, of 1/20,000 to 1/80,000.

When water in natural environment such as paddy field water and tap water is used as a sample, its reaction mixture may be prepared by adding a first antibody solution and an organic solvent directly to the sample to give predetermined concentrations, respectively. When a food, plant or soil is employed as a sample, on the other hand, its reaction mixture can be prepared by extracting, with an organic solvent, a pyrethroid compound from the sample and adding an antibody solution to the resultant extract solution, thereby preparing the reaction mixture. The reaction mixture so prepared may be incubated at 25° C. for one hour. Any unreacted portion of the first antibody in the reaction mixture is reacted with the antigen coated on a solid phase carrier by adding the reaction mixture to the carrier and then incubating the resultant carrier 25° C. for one hour. After the reaction, the carrier is washed with a washing buffer and then provided for the reaction with a second antibody.

Examples of the second antibody usable in the measuring method of the present invention include enzyme-linked antibodies against the first antibody. When a rabbit antiserum is employed as the first antibody, it is proper to use a peroxidase-labeled anti-rabbit IgG goat IgG fraction.

It is desired to conduct reaction between the first antibody bound with the carrier and the second antibody which has been diluted about 5,000–10,000-fold, preferably diluted to give the final absorbance of 1.0–1.5. A washing buffer may be employed for the dilution of the second antibody. The reaction may be carried out at 25° C. for one hour and after the reaction, the carrier may be washed with the washing buffer.

Alternatively, it is possible to use, as the second antibody, a biotin-linked antibody against the first antibody and an enzyme-labeled avidin in combination for an avidin-biotin reaction. After the first antibody bound with the carrier is reacted with a biotin-linked anti-rabbit IgG ass IgG fraction which has been diluted about 2,000-fold and the carrier is washed, it is desired to add an alkali phosphatase-labeled avidin, which has been diluted to about 1,000 fold, thereto and react them. Any other responders capable of producing the second antibody or enzymes can also be employed.

A washing buffer may be employed for the dilution. Either of the above reactions is carried out at 25° C. for one hour. After the reactions, the carrier is washed with a washing buffer and is provided for an enzymatic reaction. A reagent which develops a color by the reaction between the enzyme of the second antibody bound with the carrier and a substrate is added to the carrier and then the absorbance is measured. The amount of one or more pyrethroid compounds can be calculated from the measured absorbance on the basis of a calibration curve.

When peroxidase is used for the second antibody, hydrogen peroxide and o-phenylenediamine can be employed as the substrate and the chromogenic reagent, respectively. The chromogenic solution is added to the carrier and they are then reacted at 25° C. for 10 minutes. Immediately after the reaction, 4N sulfuric acid is added to terminate the enzymatic reaction. When o-phenylenediamine is employed, the absorbance may be measured at 492 nm and 630 nm.

When an alkali phosphatase is employed, on the other hand, color development may be carried out with p-nitrophenylphosphoric acid as a substrate. It is suited to add 2N NaOH to terminate the enzymatic reaction and measure the absorbance at 415 nm and 630 nm.

As an inhibition rate, a decreasing rate of the absorbance of a solution, which has been reacted with the antibody after the addition of a predetermined amount of one or more pyrethroid compounds, from that of a pyrethroid-compound-free solution reacted with the antibody is calculated. The concentration of the pyrethroid compound in the sample can be calculated from the inhibition rate of a reaction mixture, to which a known concentration of a pyrethroid compound has been added, based on a calibration curve.

Although the first antibodies according to the present invention differ in the degree of the reactivities, they show cross reactivities with another pyrethroid compounds in spite of the structure of the haptenic compound and can be used effectively for the general detection of pyrethroid compounds.

Examples of the pyrethroid compound detectable according to the present invention include cyclopropanecarboxylic acid esters such as resmethrin, kadethrin, cyhalothrin, biphenthrin, fenpropathrin, allethrin and tralomethrin; aromatic-substituted alkanecarboxylic acid esters such as fenvarerate, flucythrinate, fluvalinate and cycloprothrin; and non-ester compounds such as etofenprox, halfenprox (MTI-732), 1-(3-phenoxyphenyl)-4-(4-ethoxyphenyl)-4-methylpentane (MTI-790), 1-(3-phenoxy-4-fluorophenyl)-4-(4-ethoxyphenyl)-4-methylpentane (MTI-800), dimethyl-(4-ethoxyphenyl)-(3-phenoxybenzyloxy)silane (SSI-116), silafluofen and PP-682.

Total residual amount of various pyrethroid compounds in the analysis sample can be detected by the ELISA method employing both antibodies. If the analysis sample used or sprayed contains only one pyrethroid compound, the measuring result coincides with the residual amount of the corresponding compound. Even in the case of the analysis sample which contains several pyrethroid compounds, it is possible to measure their respective residual amounts by making use of an existing technique such as liquid chromatography and subjecting the sample to differential operation.

A preparation process of an antibody against etofenprox, which is used as a pyrethroid compound to be detected, and a detection method of the pyrethroid compound employing the antibody will hereinafter be described by specific examples. It is to be noted that these examples are merely illustrative and are not intended to limit the present invention thereto.

EXAMPLE 1

Synthesis of an intermediate for the haptenic compound (I)

3-Phenoxybenzyl 2-(4-hydroxyphenyl)-2-methylpropyl ether (3.0 g), 0.36 g of sodium hydride and 20 ml of acetonitrile were heated under reflux for about 20 minutes, followed by the dropwise addition of 2 ml of methyl bromoacetate at room temperature. The resulting mixture was stirred at 60° C. for 20 minutes. After concentration of the reaction mixture, about 50 ml of ethyl acetate were added to the concentrate, followed by washing with water, drying and concentration. The resulting concentrate was fractionated and purified by chromatography on a silica gel column, whereby 3.0 g of 3-phenoxybenzyl 2-{4-(methoxycarbonylmethyloxy)phenyl}-2-methylpropyl ether were obtained.

NMR: $\delta_{TMS}(CDCl_3)$ (ppm): 1.30(6H,s), 3.40(2H,s), 3.79(3H,s), 4.43(2H,s), 4.59(2H,s), 6.81–7.35(13H,m)

IR: $v_{MAX}$(neat) (cm$^{-1}$): 1763, 1585, 1488, 1252, 1213, 1080

Refractive index: 1.5641 (21.6° C.)

EXAMPLE 2

Synthesis of the haptenic compound (I)

For 2.5 hours, 2.2 g of 3-phenoxybenzyl 2-{4-(methoxycarbonylmethyloxy)phenyl}-2-methylpropyl ether, which had been obtained in Example 1, 2.5 g of sodium hydroxide, 7.5 g of water and 10 ml of ethylene glycol were heated under reflux. Dilute hydrochloric acid was added to the reaction mixture to make it acidic, followed by extraction with ethyl acetate. The extract was washed with water, dried and then concentrated. The resulting concentrate was fractionated and purified by chromatography on a silica gel column, whereby 0.9 g of 3-phenoxybenzyl 2-(4-(hydroxycarbonylmethyloxy)phenyl 2-methylpropyl ether was obtained.

NMR: $\delta_{TMS}$(CDCl$_3$) (ppm): 1.30(6H,s), 3.41(2H,s), 4.43(2H,s), 4.62(2H,s), 6.81–7.35(13H,m), 9.10–9.90 (1H, br)

IR: $\nu_{MAX}$(neat)(cm$^{-1}$): 3041, 1733, 1585, 1488, 1250, 1188, 1076

Refractive index: 1.5680 (21.6° C.)

EXAMPLE 3

Synthesis of an intermediate for a haptenic compound (II)

3-(4-Hydroxyphenoxy)benzyl 2-(4-ethoxyphenyl)-2methylpropyl ether (1.1 g), 0.17 g of sodium hydride and 10 ml of acetonitrile were stirred at 60° C. for about 20 minutes, followed by the dropwise addition of 1 ml of ethyl bromoacetate at room temperature. The resulting mixture was stirred at 50° C. for 30 minutes. The reaction mixture was filtered and the filtrate was then concentrated. The resulting concentrate was fractionated and purified by chromatography on a silica gel column, whereby 1.2 g of 3-{4-(ethoxycarbonylmethyloxy)phenoxy}benzyl 2-(4-(ethoxyphenyl)-2-methylpropyl ether were obtained.

NMR: $\delta_{TMS}$(CDCl$_3$) (ppm): 1.30(6H,s), 1.30(3H,t,J=6.6 Hz), 1.39(3H,t,J=6.6 Hz), 3.40(2H,s), 4.21–4.31(4H,m), 4.42(2H,s) , 4.60(2H,s) , 6.81–7.27 (12H,m)

IR: $\nu_{MAX}$(neat) (cm$^{-1}$): 1759, 1505, 1248, 1192, 1085

Refractive index: 1.5461 (20.4° C.)

EXAMPLE 4

Synthesis of the haptenic compound (II)

For 1.5 hours, 1.2 g of 3-{4-(ethoxycarbonylmethyloxy)phenoxy}benzyl 2-(4-(ethoxyphenyl)-2-methylpropyl ether, which had been obtained in Example 3, 0.9 g of sodium hydroxide, 3.0 g of water and 12 ml of ethyl alcohol were heated under reflux. Dilute hydrochloric acid was added to the reaction mixture to make it acidic, followed by extraction with ethyl acetate. The extract was washed with water, dried and then concentrated. The resulting concentrate was fractionated and purified by chromatography on a silica gel column, whereby 0.75 g of 3-{4-(hydroxycarbonylmethyloxy)phenoxy}benzyl 2-(4-ethoxyphenyl)-2-methylpropyl ether was obtained.

NMR: $\delta_{TMS}$(CDCl$_3$)(ppm): 1.30(6H,s), 1.39(3H,t,J=6.6 Hz), 3.40(2H,s), 4.00(2H,q,J=6.6 Hz), 4.43(2H,S), 4.66(2H, s), 6.80–7.27 (12H,m)

IR: $\nu_{MAX}$(neat) (cm$^{-1}$): 3044, 1737, 1505, 1247, 1205, 1081

Refractive index: 1.5449 (20.4° C.)

EXAMPLE 5

Synthesis of an intermediate for a haptenic compound (III)

For 4 hours, 0.9 g of 3-{4-(methoxymethyloxy)phenyloxy}benzyl chloride, 0.9 g of 2-{4-(bromodifluoromethoxy)phenyl difluoromethoxy)phenyl}-2-methylpropyl alcohol, 0.1 g of triethylbenzylammonium chloride, 3.5 g of sodium hydroxide and 4.0 g of water were stirred at 40°14 50° C. Water was added to the reaction mixture, followed by extraction with ethyl acetate. The extract was washed with water, dried and then concentrated. The resulting concentrate was fractionated and purified by chromatography on a silica gel column, whereby 1.2 g of 3-{4-(methoxymethyloxy)phenyloxy}benzyl 2-{4-(bromodifluoromethoxy)phenyl-2-methylpropyl ether were obtained.

For 2 hours, 1.2 g of 3-{4-(methoxymethyloxy)phenyloxy}benzyl 2-{4-(bromodifluoromethoxy)phenyl-2-methylpropyl ether, 0.05 g of p-toluenesulfonic acid and 30 mg of acetone were heated under reflux. The reaction mixture was concentrated, whereby 1.2 g of 3-(4-hydroxyphenyloxy)benzyl 2-{4-bromodifluoromethoxy)phenyl}-2-methylpropyl ether were obtained as an oil.

3-(4-Hydroxyphenyloxy)benzyl 2-{4-(bromodifluoromethoxy)phenyl}-2-methylpropyl ether (1.2 g), 0.13 g of sodium hydride and 10 ml of acetonitrile were stirred at 60° C. for about 20 minutes, followed by the dropwise addition of 1 ml of ethyl bromoacetate at room temperature. The resulting mixture was stirred at 50° C. for 30 minutes. The reaction mixture was filtered and the filtrate was then concentrated. The concentrate was fractionated and purified by chromatography on a silica gel column, whereby 1.0 g of 3-(4-(ethoxycarbonylmethyloxy)phenoxy}benzyl {4-(bromodifluoromethoxy) phenyl }-2-methylpropyl ether was obtained.

NMR: $\delta_{TMS}$(CDCl$_{13}$)(ppm): 1.31(3H,t,J=7.3 Hz), 1.33(6H,s), 3.43(2H,s), 4.28(2H,q,J=7.3 Hz), 4.43(2H,s), 4.61(2H,s), 6.83–7.39(12H,m)

IR: $\nu_{MAX}$(neat) (cm$^{-1}$): 1760, 1505, 1198, 1008

Refractive index: 4982 (23.8° C.)

EXAMPLE 6

Synthesis of the haptenic compound (III)

For 1.5 hours, 1.0 g of 3-{4-(ethoxycarbonylmethyloxy)phenoxy)benzyl 2-(4-(bromodifluoromethoxy)phenyl}-2-methylpropyl ether, which had been obtained in Example 5, 0.9 g of sodium hydroxide, 4.0 g of water and 20 ml of ethyl alcohol were stirred at 60° C. Water was added to the reaction mixture, followed by washing with hexane. Dilute hydrochloric acid was added to the reaction mixture to make it acidic, followed by extraction with ethyl acetate. The extract was washed with water, dried and then concentrated. The resulting concentrate was fractionated and purified by chromatography on a silica gel column, whereby 0.72 g of 3-(4-(hydroxycarbonylmethyloxy)phenoxy}benzyl 2-{4-(bromodifluoromethoxycarbonylmethyloxy)phenoxy}benzyl 2-methylpropyl ether was obtained.

NMR: $\delta_{TMS}$(CDCl$_3$) (ppm): 1.33(6H,s), 3.44(2H,s), 4.43(2H,s), 4.66(2H,s), 6.84–7.39(12H,m) IR: $\nu_{MAX}$(neat) (cm$^{-1}$): 3049, 1733, 1506, 1202, 1082, 1008

Refractive index: 1.5501 (23.5° C.)

Example 7

As immunogens, conjugates between bovine serum albumin (BSA) and the two carboxylic acid derivatives obtained in Examples 2 and 4 were prepared by the mixed acid anhydride method.

Each of the conjugates was prepared as will be described hereinafter. Twenty-five milligrams of 3-phenoxybenzyl 2-{4-(hydroxycarbonylmethyloxy)phenyl}-2methylpropyl ether, which was obtained in Example 2 and will hereinafter be called "the haptenic compound (I) and 3-{4-(hydroxycarbonylmethyloxy)phenoxy}benzyl 2-(4-ethoxyphenyl)-2-methylpropyl ether, which was obtained in Example 4 and will hereinafter be called "the haptenic compound (II), were dissolved in 2 ml of anhydrous dioxane. To the resulting solution, 0.05 ml of N-methylmorpholine was added, followed by stirring at 10° C. for 20 minutes. To the reaction mixture, 0.02 ml of isobutyl chlorocarbonate was added, followed by stirring for 15 minutes. Thus, a solution of the haptenic compound in the form of an acid anhydride was prepared.

On the other hand, 80 mg of BSA were dissolved in 4.3 ml of distilled water. The resulting solution was adjusted to pH 9.0 with a 1N solution of sodium hydroxide, followed by the addition of 2.6 ml of anhydrous dioxane in portions.

The solutions of the haptenic compounds in their acid anhydride forms, which had been prepared above, were both added to the BSA solution in portions, while maintaining the resulting solution at pH 9 with a 1N solution of sodium hydroxide, followed by reaction under stirring at 4° C. for 4 hours.

The reaction products so obtained were purified by chromatography on column employing "Sephadex G-25" (trade name), dialyzed against distilled water for 24 hours and then lyophilized for use as immunogens.

In addition, conjugates of rabbit serum albumin with the haptenic compounds (I) and (II) were also prepared as antigens in the same manner.

Each immunogen prepared above was separately dissolved in a phosphate-buffered saline [PBS; 10 mM phosphate buffer solution (pH 7.2), 0.9% NaCl ] to give a concentration of 200 µg/ml. The resulting solution was mixed with the same amount of the Freund's complete adjuvant to obtain a water-in-oil type emulsion. One milliliter of the emulsion so obtained was subcutaneously administered to a rabbit (NZW, female, 13 weeks-old).

At intervals of two weeks after the administration, the rabbit was similarly boostered with a mixed emulsion of the same immunogen and the Freund's incomplete adjuvant.

After the immunization, a blood sample collected from each rabbit was subjected to centrifugal separation to obtain its serum. The serum was salted out with 33% ammonium sulfate to provide a first antibody.

The antibody which had been obtained by immunizing with the conjugate between the haptenic compound (I) and BSA will hereinafter be designated as "antietofenprox antibody I" (abbreviated as "E-antibody I"), while the antibody which had been obtained by immunizing with the conjugate between the haptenic compound (II) and BAS conjugate will hereinafter be designated as "anti-etofenprox antibody II" (abbreviated as "E-antibody II").

EXAMPLE 8

Etofenprox was measured by the ELISA method employing E-antibody I.

1. To a 96-well polystyrene microtiter plate, a solution of the conjugate between rabbit serum albumin (RSA) and the haptenic compound (I) dissolved in a coating buffer solution [10 mM phosphate buffer solution (pH 7.5), 100 mM NaCl] to give 0.03 µl/well was added as an antigen at a ratio of 0.1 ml/well, followed by incubation at 4° C. overnight, whereby the antigen was adsorbed on the plate. After the excess solution was drained, a 3% solution of skim milk was added to the wells at a ratio of 0.3 ml/well, followed by incubation at 25° C. for one hour. The plate was washed thrice with a washing buffer [10 mM phosphate buffer solution (pH 7.2), 0.8% NaCl, 0.02% KCl, 0.02% "Tween 20"], whereby an antigen-coated plate was obtained.

2. The E-antibody I was diluted 20,000-fold with a diluting buffer [10 mM phosphate buffer solution (pH 7.5), 0.8% NaCl, 0.02% KCl] and was then mixed with a solution of etofenprox in methanol at a ratio of 1:1 to give an antibody concentration and a methanol concentration, both in the resulting solution, of 1/40,000 and 50%, respectively. The solution was reacted by incubation at 25° C. for one hour. The reaction mixture was added to the antigen-coated plate at a rate of 0.1 ml/well, followed by the reaction at 25° C. for one hour. The plate was then washed thrice with the washing buffer.

3. A conjugate between horseradish peroxidase and antirabbit IgG goat IgG (a second antibody) was diluted 10,000-fold with the washing buffer. The diluted conjugate was added to the antigen-coated plate at a rate of 0.1 ml/well, followed by incubation at 25° C. for one hour. The plate was washed thrice with the washing buffer.

4. To the antigen-coated plate, a chromogenic solution of o-phenylenediamine [0.2% (v/v) o-phenylenediamine and 100 mM phosphate-citrate buffer solution [pH 5.0, 0.003% (v/v) hydrogen peroxide] was added in an amount of 0.2 ml/well, followed by incubation at 25° C. for 10 minutes. The enzymatic reaction was then terminated by adding 4N sulfuric acid to the plate by at a rate of 0.05 ml/well. The absorbances at 492 nm and 630 nm were thereafter measured, respectively. According to this method, etofenprox concentrations ranging from 10 ng/ml to 10,000 ng/ml were successfully measured.

The ELISA method employing E-antibody II, on the other hand, will be described next. As the antigen, a 0.01 µg/ml solution of the conjugate between the haptenic compound (II) and RSA was employed. An E-antibody II solution, which had been diluted 64,000-fold, and a methanol solution of etofenprox were mixed at a ratio of 4:1 to give an antibody concentration and methanol concentration, each in the resulting solution, of 1/80,000 and 20%, respectively. The resulting solution was then reacted. As a second antibody, antirabbit IgG goat IgG in the form of a 5000-fold dilution was employed. In a similar manner to the above ELISA method, etofenprox concentrations ranging from 3 ng/ml to 1,000 ng/ml were successfully measured.

EXAMPLE 9

As was described in Example 8, the concentrations of etofenprox contained in paddy-field soil, crops (grain, vegetables, fruits or the like) and tap water were measured.

To 5 g of each of soil samples containing etofenprox at concentrations of 40–4,000 ng/ml, 5 ml of water and 15 ml of methanol were added, followed by extraction under shaking for 30 minutes. The extract was mixed with E-antibody I, which had been diluted 10,000-fold, at a ratio of 3:1. The etofenprox was measured by the ELISA method in a similar manner to Example 8.

Similarly, 10 ml of water and 30 ml of methanol were added to 10 g of each crop samples containing etofenprox at concentrations of 40–4,000 ng/ml, followed lowed by extraction under shaking for 30 minutes. The extract and the antibody, which had been diluted 10,000-fold, were mixed at a ratio of 3:1 and the concentration of etofenprox was successfully measured by the ELISA method in a similar manner to Example 8.

On the other hand, 80 mE of tap water samples containing etofenprox at concentrations of 30–3,000 ng/ml, 200 ml of an E antibody II solution, which had been diluted 40,000-fold, and 80 ml of methanol were mixed and reacted at 25° C. for one hour to give an antibody concentration and a methanol concentration, each in the reaction mixture, of 1/80,000 and 20%. The concentration of etofenprox was successfully measured by the ELISA method.

In accordance with the above method, the concentration of etophenprox in soil and crop was measurable in a range of from 40 to 4,000 ng/ml and that in tap water in a range of from 30 to 3,000 ng/ml.

EXAMPLE 10

In a similar manner to Example 8, the conjugate of the haptenic compound I or II with RSA was coated as an antigen on a 96-well microtiter plate and then, the E antibody I or E antibody II which had been reacted with etofenprox in the sample was reacted with the antigen. Etofenprox was successfully detected in accordance with the following method.

Namely, a conjugate of anti-rabbit IgG ass IgG with biotin was diluted 2,000-fold with a washing buffer. The diluted solution was added to the plate at a rate of 0.1 mE/well, followed by incubation at 25° C. for one hour. The plate was then washed thrice with the washing buffer. A conjugate of avidin with alkali phosphatase was diluted 1,000-fold with the washing buffer, followed by the addition to the plate at a rate of 0.1 ml/well and reaction at 25° C. for one hour. The plate was then washed thrice with the washing buffer.

To the plate, a chromogenic solution of alkali phosphatase [0.1% p-nitrophenylphosphoric acid, 9.7% diethanolamine-hydrochloride buffer solution (pH 9.8), 0.005% magnesium chloride] was added at a rate of 0.2 ml/well, followed by incubation at 25° C. for 30 minutes to cause color development. The reaction was thereafter terminated by adding 2N sodium hydroxide to the plate at a rate of 50 µ/well and absorbances at 415 nm and 630 nm were measured.

According to the above avidin-biotin method, 10 ng/ml or more of etofenprox was successfully measured.

EXAMPLE 11

Employing the E antibody I and E antibody II separately, their cross reactivity against various pyrethroid compounds was measured in a manner described in Example 8.

A solution of each of various pyrethroid compounds in methanol (having a concentration of 2–20,000 ng/ml) was mixed with a solution of the E antibody I, which had been diluted 20,000-fold with a diluting buffer, at a ratio of 1:1, followed by incubation at 25° C. for one hour.

Using the reaction mixture, measurement was conducted by the ELISA method as described in Example 8. The absorbance of the reaction mixture which had been obtained without addition of any pyrethroid compound is designated as 100%. The concentration of etophenprox. which inhibited 50% of the absorbance is designated as $IC_{50}$ concentration. The inhibition rates of other pyrethroid compounds when the inhibition rate of ethophenprox at $IC_{50}$ concentration is designated as 100% are shown as cross reactivity in Table 1.

In addition, solutions of each of various pyrethroid compounds in methanol (concentration: 5–50,000 ng/ml) were each mixed with an E antibody II solution, which had been diluted 64,000-fold, at a ratio of 1:4, followed by incubation at 25° C. for one hour. The reaction mixture was treated as described in Example 8 and its cross reactivity was obtained.

The inhibition rates of other pyrethroid compounds when the inhibition rate of ethophenprox at $IC_{50}$ concentration is designated as 100% are also shown as cross reactivity in Table 1.

TABLE 1

Cross reactivities of anti-etofenprox antibodies I and II to various pyrethroid compound

| Compound | Cross reactivity (%) | |
|---|---|---|
| | E antibody I | E antibody II |
| Resmethrin | 74 | 85 |
| Kadethrin | 62 | 164 |
| Cyhalothrin | 92 | 36 |
| Biphenthrin | 86 | 81 |
| Fenpropathrin | 136 | 48 |
| Allethrin | 46 | 54 |
| Tralomethrin | 116 | 67 |
| Fenvarerate | 47 | 50 |
| Flucythrinate | 126 | 60 |
| Fluvalinate | 70 | 23 |
| Cycloprothrin | 103 | 54 |
| Halfenprox | 85 | 75 |
| MTI-790 | 23 | 37 |
| MTI-800 | 54 | 34 |
| SSI-116 | 70 | 103 |
| Silafluofen | 57 | 32 |
| Flufenprox | 108 | 74 |

What is claimed is:

1. A haptenic compound of the formula (1) or (2) below:

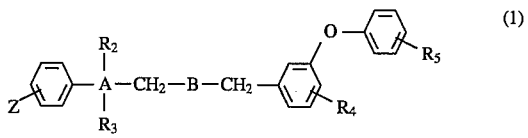

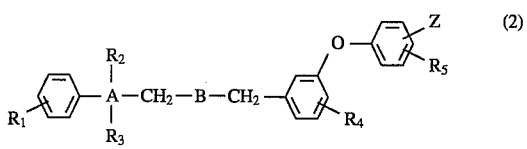

wherein $R_1$ represents a hydrogen atom, halogen atom, $C_{1-5}$ alkyl group, $C_{1-5}$ haloalky group, $C_{1-5}$ alkoxyl group, $C_{1-5}$ haloalkoxyl group, $C_{1-5}$ alkylthio group, $C_{1-5}$ haloalkylthio group, $C_{2-5}$ alkenyl group, $C_{2-5}$ haloalkenylthio group, $C_{2-5}$ alkinyl group, $C_{2-5}$ haloalkinyl group, lower-alkoxy-lower-alkyl group, lower-alkoxyl-lower-alkoxyl group, $C_{2-5}$ haloalkenyloxy group, $C_{2-5}$ alkinyloxy group, $C_{1-5}$ alkoxycarbonyl group, $C_{1-5}$ haloalkoxycarbonyl group, $C_{3-6}$ cycloalkyl group, $C_{3-6}$ cycloalkoxyl group, phenyl group, phenoxy group or cyano group; $R_2$ represents a $C_{1-5}$ alkyl group or C1–5 haloalkyl group, $R_3$ represents a hydrogen atom, $C_{1-5}$ alkyl group or $C_{1-5}$ haloalkyl group, and $R_2$ and $R_3$ may be coupled together to form a $C_{3-6}$ cycloalkyl group or $C_{3-6}$ cyclohaloalkyl group; $R_4$ and $R_5$ individually represent a hydrogen atom, halogen atom, alkyl group or alkoxyl group; A represents a carbon atom or silicon atom; B represents —$CH_2$—, —$NR_6$—, —O— or —S—; $R_6$ represents a hydrogen atom or lower alkyl group; and Z represents —Y—$(CH_2)$m-COOH or —Y—$(CH_2)$n-$NH_2$, Y represents —$H_2C$—, —$NR_7$—, —O— or —S—, $R_7$ represent a hydrogen atom or lower alkyl group, and m and n individually stand for 1–5.

2. An intermediate for the preparation of a haptenic compound as defined in claim 1, which is represented by the following formula (3) or (4)

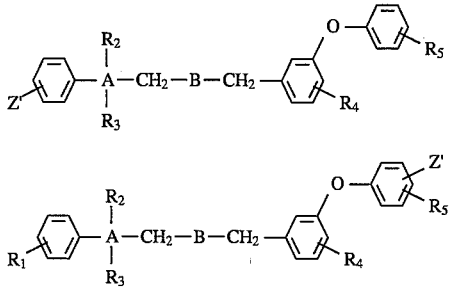

wherein $R_1$ represents a hydrogen atom, halogen atom, $C_{1-5}$ alkyl group, $C_{1-5}$ haloalkyl group, $C_{1-5}$ alkoxyl group, $C_{1-5}$ haloalkoxyl group, $C_{1-5}$ alkylthio group, $C_{1-5}$ haloalkylthio group, $C_{2-5}$ alkenyl group, $C_{2-5}$ haloalkenylthio group, $C_{2-5}$ alkinyl group, $C_{2-5}$ haloalkinyl group, lower-alkoxyl-lower-alkyl group, lower-alkoxyl-lower-alkoxyl group, $C_{2-5}$ haloalkenyloxy group, $C_{2-5}$ alkinyloxy group, $C_{1-5}$ alkoxycarbonyl group, $C_{1-5}$ haloalkoxycarbonyl group, $C_{3-6}$ cycloalkyl group, $C_{3-6}$ cycloalkoxyl group, phenyl group, phenoxy group or cyano group; $R_2$ represents a $C_{5-l}$ alkyl group or $C_{5-l}$ haloalkyl group, $R_3$ represents a hydrogen atom, $C_{5-l}$ alkyl group or $C_{5-l}$ haloalkyl group, and $R_2$ and $R_3$ may be coupled together to form a $C_{3-6}$ cycloalkyl group or $C_{3-6}$ cyclohaloalkyl group; $R_4$ and $R_5$ individually represent a hydrogen atom, halogen atom, alkyl group or alkoxyl group; A represents a carbon atom or silicon atom; B represents —$CH_2$—, —$NR_6$—, —O— or —S—; $R_6$ represents a hydrogen atom or a lower alkyl group; and Z' represents —Y'—$(CH_2)$m-COOR$_7$' or -Y'—$(CH_2)$n-NHR$_8$, Y' represents —$CH_2O$—, —$NR_9$—, —O— or —S—, $R_7$' represents a $C_{1-5}$ alkyl group, lower-alkoxyl-lower-alkyl group, lower-alkoxyl-lower-alkoxyl-lower-alkyl group, lower-alkylthio-lower-alkyl group, tetrahydropyranyl group, tetrahydrofuranyl group, phenyl group, phenyloxy-lower-alkyl group, phenacyl group, diacylmethyl group, N-phthalimido methyl group, benzyl group or silyl group; m stands for 1 to 5, $R_8$ represents a formyl, acetyl, haloacetyl, propionyl, phenylacetyl, alkoxycarbonyl, haloalkoxycarbonyl, fluorenemethylcarbonyl, phenyloxycarbonyl, phenylthiocarbonyl, piperidinyloxycarbonyl or benzyloxycarbonyl group, $R_9$ represents a hydrogen atom or a lower alkyl group, and n stands for 1 to 5.

* * * * *